United States Patent
Braun et al.

(10) Patent No.: US 7,648,698 B2
(45) Date of Patent: Jan. 19, 2010

(54) VACCINE FOR VETERINARY AND HUMAN MEDICINE PROPHYLAXIS AND THERAPY

(75) Inventors: Dagmar Braun, Greifswald-Insel Riems (DE); Vladimir Vrzal, Ivanovice na Hané (CZ); Libor Bittner, Vyskov (CZ); Dagmar Koukalova, Olomouc (CZ)

(73) Assignee: Bioveta AG (CZ)

( * ) Notice: Subject to any disclaimer, the term of this patent is extended or adjusted under 35 U.S.C. 154(b) by 0 days.

(21) Appl. No.: 11/574,808

(22) PCT Filed: Sep. 23, 2005

(86) PCT No.: PCT/EP2005/010347
§ 371 (c)(1),
(2), (4) Date: May 8, 2008

(87) PCT Pub. No.: WO2006/032533
PCT Pub. Date: Mar. 30, 2006

(65) Prior Publication Data
US 2008/0254068 A1    Oct. 16, 2008

(30) Foreign Application Priority Data
Sep. 24, 2004    (DE) .................. 10 2004 046 391

(51) Int. Cl.
*A01N 63/04* (2006.01)
*A61K 31/38* (2006.01)
*A61K 39/00* (2006.01)
*A61K 39/02* (2006.01)
*A01N 63/00* (2006.01)

(52) U.S. Cl. ............. 424/93.51; 424/93.5; 424/274.1; 424/184.1; 424/93.4; 424/234.1; 424/93.3

(58) Field of Classification Search ............ None
See application file for complete search history.

(56) References Cited

U.S. PATENT DOCUMENTS
2003/0039667 A1    2/2003    Jira

FOREIGN PATENT DOCUMENTS
CS    277 558 B6    2/1993
WO    0232442 A1    4/2002

OTHER PUBLICATIONS

Kpukalova et al. CS 277558, 1993. English translation.*
Minamisawa et al. Applied and Environmental Microbiology 70: 3096-3102, 2004.*
Davidson et al. J. Dairy Sci. 83: 666-673, 2000.*
Koukalová, D., et al., "Experimental Nonspecific Immunostimulation by the Propionibacterium Acnes Vaccine," Acta Universitatis Palackianae Olumucensis, Facultatis Medicae 133:19-23, 1992.
Nalewak, L., et al., "Media Evaluation for the Detection of Anaerobic Microorganism in Biopharmaceutical Manufacturing Samples," 101st General Meeting of the American Society for Microbiology, Orlando, Florida, May 20-24, 2001, pp. 419-420 (abstract only).

* cited by examiner

*Primary Examiner*—S. Devi
(74) *Attorney, Agent, or Firm*—Christensen O'Connor Johnson Kindness PLLC

(57) ABSTRACT

The present invention relates to a novel vaccine, its use for immunoprophylaxis and/or the treatment of candidamycoses in human and veterinary medicine as well as methods for its preparation, wherein said vaccine consists of the combination of the *Candida* strains
a1) *Candida albicans* CCM 8355
a2) *Candida glabrata* CCM 8356
a3) *Candida krusei* CCM 8357 and
a4) an immunomudulating *Propionibacterium acnes* strain, and optionally pharmaceutically acceptable excipients, such as carriers, wherein the ratio of the components a1-a4 in the end product is a1:a2:a3:a4 is 10-20:10-20:10-20:40-70.

28 Claims, 3 Drawing Sheets

PCR characteristic of the vaccination strains

Fig. 1. PCR detection of micromycetes. 1 – *C. glabrata* (410 bp amplification product), 2 - *C. albicans* (326 bp amplification product), 3 - *C. krusei* (336 bp amplification product), M100 – 100 bp weight standard 1. Candida glabrata - CCM 8356
2. Candida albicans - CCM 8355
3. Candida krusei - CCM 8357

PCR characteristic of the vaccination strains

Fig. 2. PCR detection and RFLP identification of *P. acnes*. 1 – 370 bp PCR amplification product of *P. acnes* (519 bp fragment – internal standard), 2 – *HaeIII* restriction fragments (110 and 260 bp), 3 – *NcoI* restriction fragments (370 bp), M100 – 100 bp weight standard Propionibacterium acnes - CCM 7083

PCR characteristic of the vaccination strains

Obr. 3. PCR-RFLP identification of micromycetes.

1. Candida glabrata - CCM 8356
2. Candida albicans - CCM 8355
3. Candida krusei - CCM 8357

VACCINE FOR VETERINARY AND HUMAN MEDICINE PROPHYLAXIS AND THERAPY

FIELD OF THE INVENTION

The present invention relates to a novel vaccine, its use for immunoprophylaxis and the treatment of candidamycoses in veterinary and human medicine as well as methods for its preparation.

BACKGROUND OF THE INVENTION

Mycoses are caused by yeasts and lower fungi. Only approximately 300 varieties of the known approximately 10,000 varieties of fungi are pathogenic for humans. Their noxious effect is based, on the one hand, on the direct attack on living tissue and on the other hand, on the production of mycotoxins and their indirect effect, such as the inducement of allergies. Based on the site of infection, a differentiation is made between systemic and superficial mycoses.

*Candida* is a genus of asporogenic blastomyces with numerous possibly pathogenic species. The most common pathogens of candidiasis are, amongst others, *C. albicans, C. guilliermondii, C. krusei, C. parapsilosis, C. pseudotropicalis, C. pulcherrima, C. stellatoidea, C. glabrata* and *C. tropicalis*.

Candidamycoses are opportunistic mycoses (fungal diseases) caused by candida species, mostly by *Candida albicans*, which can manifest as cutaneous or mucocutaneous disease, particularly as stomatitis (thrush), esophagitis, diaper erythema or vulvovaginitis. They can also manifest systemically as life-threatening generalized candidosis, especially in neonates and patients whose immunocompetence is disturbed. This occurs particularly when cytostatics or antibiotics, steroids or hormones are administered or in the case of parenteral nutrition, malignant diseases, endocrinopathies or immunodefects. Recently, the occurrence of nosocomial mycoses caused by *Candida* has increased significantly (see e.g. Doležal, Česká a Slovenská farmacie, Vol. LI, 5$^{th}$ edition, September 2002, p. 226-235) and these mycoses are an important cause of the morbidity and the mortality particularly of hospital inpatients.

While there is a large choice of active substances for the treatment of superficial mycoses, the possibilities for treating systemic mycoses are very limited.

The role of genetic engineering in the development of new therapeutic agents against fungal infections is summarized in the article by Korabečná et al., Epidemiol. Microbiol. Immunol., 52, 2003, No. 1, p. 25-33.

As already described above, the occurrence of fungal infections has increased dramatically over the last years. This is in particular due to the continuously increasing number of patients having a suppressed immune system, such as transplant recipients, cancer and HIV patients. On the other hand, the wide spread use of broad-spectrum antimycotics has resulted in a great number of resistant pathogen strains, which further aggravates the situation (see e.g. Jarvis et al., Clinical Infectious Disease, 1995, 20, p. 1526-30; Beck-Sague et al., The Journal of Infectious Disease, 1993, 167, p. 1247-51; Gottfredson et al., Pathology, 30, 1998, p. 405-418; Tom šiková et al., Epidemiol. Microbiol. Immunol., 51, 2002, No. 3, p. 119-124; Rex et al., Antimicrob. Agents Chemother., 39, 1995, p. 1-8; Kunová, Epidemiol. Microbiol. Immunol., 51, 2002, No. 3, p. 131-134).

The most frequent fungal infection in humans, however, is a vaginal fungal infection. In this context, it is problematic that such infections very often become chronic and that in these cases antimycotics, which are administered locally and mostly over a longer period of time, often remain without effect.

The preparation of therapeutic agents against mycoses on an immunological basis is dealt with, amongst others, in Bernardis et al., Infection and Immunity, February 1994, p. 509-519; Bernardis et al., Infection and Immunity, August 1997, p. 3399-3404; de Bernardis et al., Infection and Immunity, June 2000, p. 3297-3304; Martinez et al., Clinical Microbiology Reviews, January 1998, p. 121-141; Polonelli et al., Med. Mycol., 2000, 38, Suppl. 1: 281-292; Medling et al., Mycoses, 1966, 39, p. 177-183 and Odds F. C. in *Candida and Candidosis*; 2$^{nd}$ ed. 1988, Baillière Tindal W. B. Saunders, London.

Hence, for some time, intensive efforts have been made to develop a vaccine against fungal infections, in particular against *Candida* infections. The approaches are manifold.

Thus, CS 277 558 describes a vaccine for peroral and/or local treatment of chronic vaginitis and other chronic mucosal inflammations caused by yeasts wherein the vaccine can also be used in combination with antimycotics. This vaccine contains 3 *Candida albicans* strains (CA 37, CA 91 and CA 120), a *Candida krusei* strain (CK 9), a *Candida glabrata* strain (TG 15) and 3 *Propionibacterium acnes* strains (PA 3, PA 17 and PA 530).

RU 2185842 describes a preparation from *Bacillus subtilis* optionally in combination with *Bifidobacterium bifidum* and/or *Lactobacilli* strains for the treatment of urogenital infections that are caused, amongst others, by *Candida*.

U.S. Pat. No. 5,578,309, US 2002/0160009A1 and WO 00/52053 describe the use of phosphomannan from *Candida albicans* for the therapy of *Candida* infections and also, amongst others, the use of monoclonal antibodies for passive immunisation against *Candida* infections.

A vaccine without adjuvant, which is to be applied enterally and contains killed microorganisms capable of infecting the vagina, such as *Candida albicans, Gardnerella vaginalis, Neisseria gonorrhoea, Trichomonas vaginalis* or *Herpes genitalis* is disclosed in WO 96/07426.

U.S. Pat. No. 6,099,853 describes, amongst others, a formulation for the treatment of urogenital infections in form of a suppository containing 8 to 14 different inactivated uropathogenic bacteria strains of the species *Escherichia coli, Klebsiella pneumoniae, Proteus mirabilis, Proteus morganii* and *Streptococcus faecalis*.

Antibody and antigen containing microparticles for passive or active immunisation of the female genital tract are the subject matter of U.S. Pat. No. 4,732,763. U.S. Pat. No. 5,288,639 describes the use of a polypeptide sequence from *Candida* having high homology to known stress proteins of other organisms and antibodies produced therewith for the therapy and diagnosis of mycoses, in particular of *Candida* mycoses.

U.S. Pat. No. 4,678,748, on the other hand, discloses a method for the production of immune biological preparations for the diagnosis, prophylaxis and/or therapy of *Candida guilliermondii* infections.

DETAILED DESCRIPTION OF THE INVENTION

Figure 1:
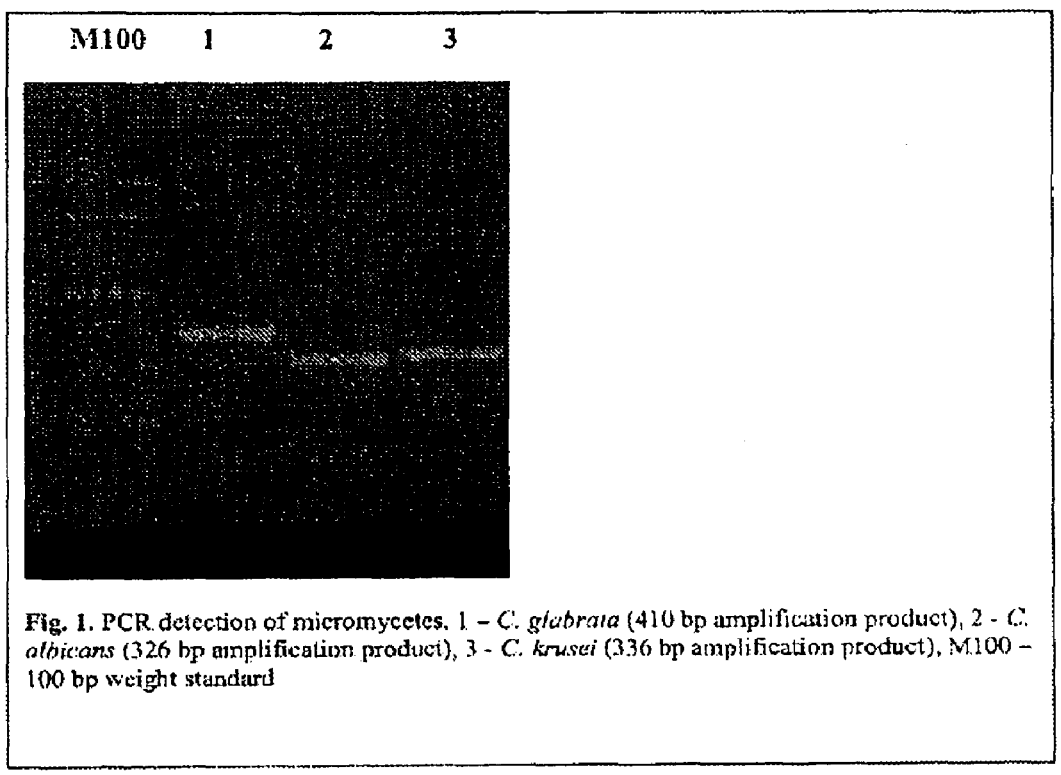
FIG. 1 illustrates PCR detection of micromycetes; Lane 1—410 bp PCR amplification product of *Candida glabrata* (strain CCM 8356), Lane 2—326 bp PCR amplification product of *Candida albicans* (strain CCM 8355), Lane 3—336 bp PCR amplification product of *Candida krusei* (strain CCM 8357), and M100-100 bp molecular weight standard.

The present invention first relates to a novel vaccine containing a combination of the *Candida* strains a1) *Candida albicans* CCM 8355
a2) *Candida glabrata* CCM 8356
a3) *Candida krusei* CCM 8357 and
a4) an immunomodulating *Propionibacterium acnes* strain, and optionally one or more excipients such as vehicles, filling agents or carriers, wherein the ratio of the components a1-a4 in the final product is a1:a2:a3:a4=10-20:10-20:10-20:40-70.

Further, the present invention relates to methods for the preparation of vaccines according to the invention.

The vaccines according to the invention are used in human as well as in veterinary medicine.

According to the invention, *Candida* mycoses (Candidiasis) refer to a disease caused by fungi of the genus *Candida*. As described above, it may occur locally as well as systemically.

Thus, the present invention provides a vaccine for prophylaxis and/or treatment of local, cutaneous or mucocutaneous and/or systemic candidiasis.

In this connection, the local candidiasis may relate to the outer mucosa of the genital tract, the urogenital tract, the oral cavity, the gastrointestinal tract, the mammary glands, the auditory canal or the skin.

In particular, stomatitis (thrush), esophagitis, diaper erythema, pyodermitis pustulosa, folliculitits, erythematosquamous form, intertrigo, phlebitis, granulomatous candidosis, granuloma, onychia, paronychia, erosio interdigitalis candidomycetica, maduramycosis (in particular of the leg), vulvovaginitis, abscess after injections, complications after burns, angular cheilitis (perlèche), glossitis, lingua pilosa nigra, hyperplastic lingual candidiasis, oral leukoplakia, tonsillocandidiasis, keratitis, endophthalmitis, corneal ulcer, otitis and balanitis are comprised.

The systemic candidiasis, the treatment of which and the prophylaxis against which is possible with the vaccine of the invention, includes, amongst others, generalized systemic candidosis, candidemia, acute hematogenic disseminated candidiasis, chronic disseminated candidiasis, *Candida* endocarditis, *Candida* pericarditis, purulent phlebitis, *Candida* meningitis, *Candida* pneumonia, *Candida* osteomyelitis, *Candida* mediastinitis, *Candida* arthritis, *Candida* gastritis, *Candida* colitis, interstitial candidiasis, peritonitis, angiolitis, oropharyngeal and esophageal candidiasis, renal moniliasis, uretritis, cystitis pseudomembranacea, mycetoma, renal abscess, *Candida* bronchitis, *Candida* bronchopneumonia, primary bronchial candidiasis, primary lung candidiasis, *Candida* meningoencephalitis, cerebral abscesses or ocular damages caused by disseminated primary systemic candidiasis; furthermore, also allergy-induced diseases such as bronchial asthma, bronchitis, rhinitis, eczema, farmer's lung and similar syndromes.

Preferably, the immunomodulating *Propionibacterium acnes* strain is *Propionibacterium acnes* CCM 7083. Further immunomodulating *Propionibacterium acnes* strains tested are *Propionibacterium acnes* PA3 and *Propionibacterium acnes* PA 530.

Further, a vaccine is preferred in which the ratio a1:a2:a3:a4 is 15-20:15-20:15-20:40-55 or 10-15:10-15:10-15:55-70. Particularly preferred, the ratios are a1:a2:a3:a4=10:10:10:70 and 20:20:20:40 or 15:15:15:55. A ratio of a1:a2:a3:a4=10:10:10:70 for oral application, a ratio of a1:a2:a3:a4=15:15:15:55 for vaginal application and a ratio of a1:a2:a3:a4=20:20:20:40 for rectal application is even more preferred.

The vaccine according to the invention contains preferably 2 to 10 mg of total dry weight of the vaccine strains a1 to a4 per dosage.

The total content of formaldehyde in the final product is preferably less than 0.02% by weight.

The vaccines of the invention can be formulated by the person skilled in the art in dosage forms for parenteral, local or oral application using methods known per se, e.g. according to Remington's Pharmaceutical Sciences, 15$^{th}$ ed.

In this context, the topical, vaginal or rectal application is particularly preferred.

Dosage forms of the vaccine of the invention comprise in particular (hard) capsules, tablets, lozenges, pastilles, syrups, oral suspensions, oral emulsions, globuli, pills, rectal suppositories, vaginal suppositories, vaginal ovula, ampoules, prefilled syringes, aerosols, insufflations and mouth-washes.

Excipients used according to the invention comprise, for example, diluents, carriers, vehicles, preservatives, colourants, disintegrants, binding agents, emulsifying agents, solubilising agents, netting agents, solvents, buffering agents, gel-forming agents, thickening agents, film-forming agents, glidants, lubricants, form-separating agents, flow-regulating agents, sorbents, antioxidants as well as flavour and odour correctives.

The bases for suppositories and vaginal ovula include lipid-containing and water-soluble preparations, with, in particular, cocoa butter, hardened fat, macrogol 6000, PEG 6000 or mixtures of macrogols or glycerine gelatine being used.

When formulating dosage forms for oral application, in particular, aerosil, saccharose, starch, particularly potato starch, or mixtures of at least two of the aforementioned are used as carriers/vehicles.

The vaccine of the invention can be used as well in human as in veterinary medicine for prophylaxis and/or therapy of local or systemic candidiasis, such as e.g. dermatomycoses, pneumomycoses, enteromycoses, or deep mycoses, such as chromomycosis, maduramycosis, keloid blastomycosis, phycomycosis, blastomycosis or coccidioidomycosis.

Due to the broad composition with regard to the antigens, the vaccine of the invention is capable of not only inducing immunity against homologous *Candida* strains but also of evoking a cross-reaction against other mycosis pathogens, such as for example blastomycetes like *Cryptococcus neoformans*, molds like *Aspergillus flavus, Aspergillus parasiticus, Aspergillus niger, Aspergillus fumigatus, Aspergillus terreus, Fusarium oxysporum, Mucor plumbeus, Mucor rouxii, Absidia corymbifera, Emericella nidulans, Alternaria solani, Alternaria alternate, Malassezia pachydermatis, Malassezia furfur, Saccharomyces cerevisiae*, and *Rhodotorula rubra*; dimorphic fungi like *Candida dubliniensis, Candida lipolytica, Candia zeylanoides, Candida pelliculosa, Candida lusitaniae, Candida kefyr, Candida parapsilosis, Candida tropicalis* and *Candida guilliermondii*, and dermatophytes like *Trychophyton verrucosum, Trychophyton rubrum, Tricho-*

*phyton mentagrophytes, Microsporum canis* and *Trichophyton equinum*, and, thus, it is capable of providing protection.

The *Propionibacterium acnes* strain of the invention has a significant unspecific immunostimulating effect and, thus, it has a positive effect on the formation of the specific immune response and, consequently, it leads to an overall enhancement of the immune response.

Moreover, the vaccine of the invention may be administered in combination with other pharmaceutical compositions such as antimycotics or antibiotics. This can be done simultaneously, consecutively at certain time intervals or as a specific therapeutic regime.

The vaccine strains a1 to a3 used pertain to the genus *Candida*, cultures of the strains *Candida albicans* CCM 8355 (a1), *Candida glabrata* CCM 8356 (a2) and *Candida krusei* CCM 8357 (a3) have been deposited by the applicants with the CCM—Czech Collection of Microgorganisms, Masaryk University, Tvrdeho 14, 620 00 Brno, Czech Republic on 23 Jan. 2003 according to the Budapest Treaty under the accession numbers CCM 8355, CCM 8356 and CCM 8357, respectively.

Moreover, the use of *Propionibacterium acnes* CCM 7083, the immunomodulating *Propionibacterium acnes* strain, as vaccine strain a4 is preferred. Cultures of *Propionibacterium acnes* CCM 7083 have also been deposited by the applicants with the CCM—Czech Collection of Microorganisms, Masaryk University, Tvrdeho 14, 620 00 Brno, Czech Republic on 23 Jan. 2003 according to the Budapest Treaty under the accession number CCM 7083.

Due to the selection of the *Candida* strains and of the immunomodulating *Propionibacterium acnes* strain in the optimised mixing ratio of the invention, the vaccines of the invention have a positive effect on the immune system of the patient and can be used for both the prophylaxis and the therapy of existing local and systemic *Candida* mycoses.

Even though a very large number of pathogen *Candida* and *Propionibacterium* strains are known, in general, with the exception of few strains, no immunomodulating or immunostimulating effect could be detected in different in vivo animal models. Surprisingly, the vaccine strains of the invention had, however, a positive effect on the immune system.

The strains are characterised further as follows:

1.1 *Candida* Strains a) Assimilation

| Test assimilation of | *Candida albicans* CCM 8355 | *Candida krusei* CCM 8357 | *Candida glabrata* CCM 8356 |
|---|---|---|---|
| Galactose | + | − | − |
| Maltose | + | − | − |
| Saccharose | + | − | − |
| Xylase | + | − | − |
| Adonitol | + | − | − |
| Citrate | + | + | − |
| Erythritol | + | − | − |
| Mannitol | + | − | − |
| Sorbase | − | − | + |
| Amylum | + | − | − |
| Trehalose | + | − | + | b) Fermentation Activity

| Test fermentation of | *Candida albicans* CCM 8355 | *Candida krusei* CCM 8357 | *Candida glabrata* CCM 8356 |
|---|---|---|---|
| Galactose | − | − | − |
| Maltose | + | − | − | c) Further Characterisation of the Strains

| Test | *Candida albicans* CCM 8355 | *Candida krusei* CCM 8357 | *Candida glabrata* CCM 8356 |
|---|---|---|---|
| Formation of | | | |
| Chlamydospores | + | − | − |
| pseudomycelium | + | + | − |
| Resistance vis-à-vis | | | |
| Actidion (cycloheximide) | + | − | − |
| NaIO$_4$ | + | − | + |
| Tolerance vis-à-vis | | | |
| pH 1.55 | + | + | − |
| pH 1.4 | + | − | − |
| Growth on McConkey agar | − | + | + |
| Serotype | A | not defined | not defined |

All the selected *Candida* strains grew at 37° C. and were resistant against sodium chloride and boric acid. The strains neither produced arthrospores nor capsules, pigments, phenoloxidase or proteinase.

1.2 *Propionibacterium* Strain

| Test | *Propionibacterium Acnes* CCM 7083 |
|---|---|
| Digestion of | |
| fructose | − |
| galactose | − |
| glucose | + |
| Hydrolysis of gelatine | − |
| Coagulation of milk | − |
| Reduction of nitrates | + |

The selected *Propionibacterium* strain was catalase positive (i.e. it produced catalase), penicillin-susceptible and produced indol. The strain was immobile and digested neither lactose, nor maltose, mannitol, rhamnose, saccharose, salicin, trehalose or esculin. The strain neither produced lecitinase nor lipase, urease or pigment. Predigestion of milk was also not observed.

Figure 2:
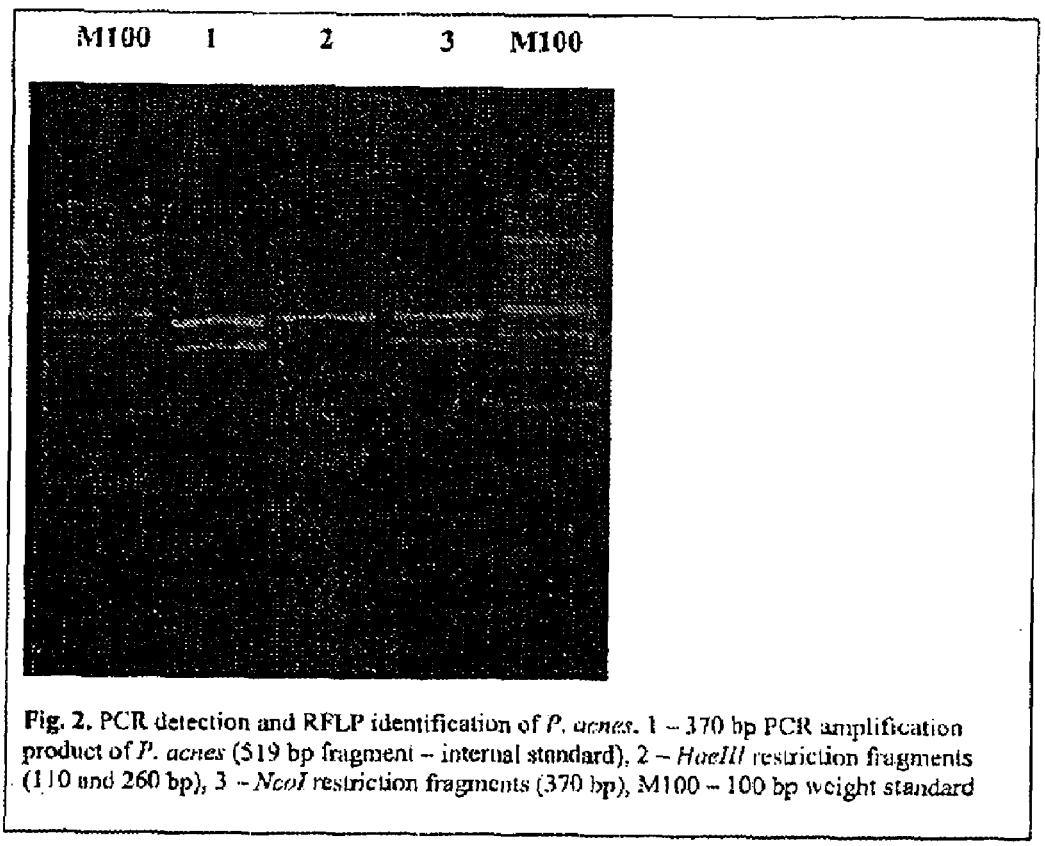
FIG. 2 illustrates PCR detection and RFLP identification of *P. acnes* (production strain (CCM 7083); Lane 1—370 bp PCR amplification product of *P. acnes* (519 bp fragment—internal standard), Lane 2—HaeIII restriction fragments (110 and 260 bp), Lane 3—NcoI restriction fragments (370 bp), and M100-100 bp molecular weight standard.
Figure 3:
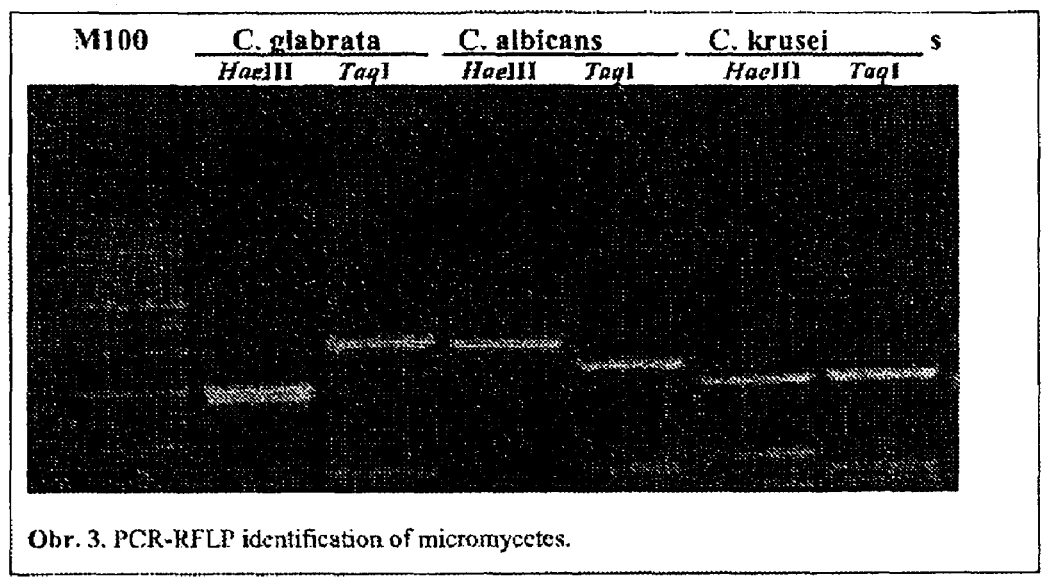
FIG. 3 illustrates PCR-RFLP identification of micromycetes using restriction enzymes HaeIII and TaqI. The production strains include *Candida glabrala* (strain CCM 8356), *Candida albicans* (strain CCM 8355), and *Candida krusei* (strain CCM 8357).

FIGS. 1-3 show the PRC characterisation of the 4 vaccine strains.

Moreover, the present invention relates to the a method for the preparation of the vaccine of the invention, comprising the following steps:

1) separately cultivating the vaccine strains a1 to a4 and isolating the cellular mass;
2) inactivating the *Candida* strains a1 to a3 by means of formaldehyde;
3) heat-inactivating the *Propionibacterium acnes* strain a4;
4) separately lyophilising the strains a1 to a4; and
5) mixing the vaccine strains with optionally one or more excipients, carriers, vehicles; and
6) optionally formulating a dosage form.

Other possible methods for inactivating the vaccine strains are, amongst others, the chemical inactivation such as e.g. with betapropiolacton.

In a preferred method of the invention, in step 1), the *Candida* strains a1 to a3 are cultivated separately on glucosopeptone agar at 23 to 27° C. for 48 to 72 hours or on Sabouraud agar at 35 to 39° C. for 22 to 27 hours under aerobic conditions, isolated and, subsequently, washed with sterile water for injection and broken up in three freeze and thaw cycles.

In a further preferred method of the invention, in step 1), the *Candida* strains a1 to a3 are separately cultivated in Sabouraud medium at 37° C. for 24 to 48 hours under aerobic conditions.

Subsequently, the bacteria cells are isolated using an ultrafiltration cartridge with a cut-off of 300 kDa and purified by repeated washing with sterile physiologic saline and centrifugation at 4,500 g (e.g. Jouan KR 22, 5,000 rpm). The isolated bacteria cells are then washed with sterile water for injection and disintegrated in three freeze and thaw cycles (at least −20° C.). Instead of disintegrating the vaccine strains a1 to a3 by means of freeze and thaw cycles, the disintegration can be carried out by means of ultrasound.

In a further preferred method of the invention, in step 1), the *Propionibacterium acnes* strain a4 is cultivated on a blood agar, a Reinforced *Clostridium* Agar or in a VL agar with blood at 35 to 39° C. for 46 to 50 hours under strict anaerobic conditions, isolated and, subsequently, washed with sterile water for injection and lysed, extracted at 2 to 8° C. for 22 to 26 hours and, in step 3), inactivated by heating it up to 56 to 62° C. three times for one hour at an interval of at least 24 hours.

In a further preferred method of the invention, in step 1), the *Propionibacterium acnes* strain a4 is cultivated in Reinforced Clostridial Medium at 35 to 39° C. for 46 to 50 hours under strict anaerobic conditions under static conditions and the bacteria cells are isolated using an ultrafiltration cartridge with a cut-off of 300 dKa. Subsequently, a purification is carried out by repeated washing with physiological saline and centrifugation at 4,500 g (e.g. Jouan KR 22, 5,000 rpm), followed by lysis with sterile water for injection and extraction at 2 to 8° C. for 22 to 26 hours. In step 3), the bacterial material is inactivated by heating it up to 56 to 62° C. three times for one hour at an interval of at least 24 hours.

In a particularly preferred method of the invention, in step 1), strains a1 to a4 are cultivated separately in a fermenter/bioreactor, preferably continuously, and subsequently, isolated. A bioreactor which is usable according to the invention is e.g. APPLIKON ADI, 270 liters.

Here, it is preferred that the *Candida* strains a1 to a3 are cultivated in a sterile fluid Sabouraud medium under aerobic conditions, at 0.1-0.2 bar, at 15-20% $O_2$, at a pH of 5.6 to 7.2, at 23 to 27° C., at 40-50 rpm for 16 to 24 hours.

Preferred cultivation conditions in a bioreactor/fermenter for the *Propionibacterium acnes* strain a4 consist in cultivating under anaerobic conditions, at 0.1-0.2 bar under addition of a mixture of N:$CO_2$ (1:2) of approx. 10 l/min., at a maximum of 1% $O_2$ at a pH of 6.4 to 7.2 for a period of 15 to 17 hours at 35 to 39° C. in a fluid modified Reinforced *Clostridium* Medium at 40 to 50 rpm.

If the cultivation is carried out in a fermenter/bioreactor, the isolation of the cellular mass is preferably carried out by industrial ultracentrifugation at 3,600 g to 5,300 g or by ultrafiltration.

Other possible methods for the inactivation of the vaccine strains are, amongst others, the chemical inactivation, such as e.g. with betapropiolacton.

As can clearly be seen from the application examples in the animal models and in human medicine, the present invention provides a highly effective vaccine which, moreover, can be applied easily, as a parenteral application is not necessary.

EXAMPLES OF PRODUCTION AND APPLICATION

Example of Production 1

Production of a Vaccine for Oral Application

A Sabouraud agar was used for the cultivation of the *Candida* strains a1 to a3, which had been sterilised at an overpressure of 80 to 100 kPa for 20 to 30 min. After the pH had been adjusted to 6.0 to 6.9, the agar was poured into glass Petri dishes and was once again sterilised under the same conditions. The Petri dishes with the solidified culture medium were examined for sterility and separately inoculated with the individual *Candida* strains a1 to a3. To this aim, lyophilisates or fresh inoculates were used which were distributed on the surface of the culture media and, subsequently, cultivated at 23 to 27° C. for 48 to 72 hours under aerobic conditions at normal pressure and an atmospheric humidity of 90-98% until optimum growth was achieved (determined by OD-measuring at 605 nm using a spectrometer in Br). The cultures were then harvested with sterile water for injection from the surface of the culture media and disintegrated in three freeze and thaw cycles (at least −20° C.). The lysate obtained was inactivated by addition of aqueous formaldehyde solution. The total formaldehyde content of the final product was less than 0.02% by weight. Following a test for sterility, the inactivated lysate of the *Candida* strains was lyophilisated for 48 hours until the residual water content preferably was less than 3%.

Reinforced Clostridial Agar was used for the cultivation of the *Propionibacterium acnes* vaccine strain. The culture medium was sterilised in an autoclave at an overpressure of 80 to 100 kPa for 20 to 30 min. After adjusting the pH to 6.6 to 7.0, the medium was filled into glass Petri dishes and was once more sterilised under the same conditions. The solidified culture media were examined for sterility and inoculated with cultures of the *Propionibacterium acnes* vaccine strain. The vaccine strain was distributed on the surface of the culture medium and cultivated at 35 to 39° C. for 46 to 50 hours under strict anaerobic conditions until growth reached an optimum. The cultures were harvested in the phase of the highest antigen production (determined by OD-measuring at 605 nm using a spectrometer in Br) by using sterile water for injection and were extracted at 2 to 8° C. for 22 to 26 hours. The cellular mass obtained was inactivated by heating it up to 56 to 62° C. three times for one hour at an interval of at least 24 hours. Following a test for sterility, the inactivated cellular mass was lyophilised for 48 hours until a residual water content of preferably less than 3% was obtained.

After lyophilisation, the strains were mixed in a carrier consisting of a mixture of aerosil, saccharose and potato starch or another suitable vehicle so that the final product contained the strains in a ratio of a1:a2:a3:a4=10:10:10:70.

The mixture obtained in this way was filled in (hard) capsules for oral application with each capsule containing 2 mg vaccine strains and 248 mg carrier/vehicle. The final product was checked for microbiological purity, residual water content, solubility and formaldehyde content.

During experimental application in mice, the vaccine induced a strong specific humoral and cellular immune response as demonstrated further below.

Example of Production 2

Production of a Vaccine for Vaginal Application

The strains to be used were cultivated in the manner described in Example 1.

After lyophilisation, the strains were mixed with melted cocoa butter so that the final product contained the strains in a ratio of a1:a2:a3:a4=15:15:15:55 and vaginal suppositories were produced in a known manner.

A vaginal suppository contained 6 mg vaccine strains (dry weight) and 3 g cocoa butter (or another basis).

The final product was checked for microbiological purity, solubility and formaldehyde content.

The experimental application in mice also led to the properties shown in Example 1.

Example of Production 3

Production of a Vaccine for Rectal Application

The strains to be used were cultivated in the manner described in Example 1. After lyophilisation, the strains were mixed with melted cocoa butter so that the final product contained the strains in a ratio of a1:a2:a3:a4=20:20:20:40 and rectal suppositories were produced in a known manner.

A rectal suppository contained 10 mg vaccine strains (dry weight) and 3 g cocoa butter (or another conventional basis).

The final product was checked for microbiological purity, solubility and formaldehyde content.

The experimental application in mice also led to the properties shown in Examples 1 and 2.

Example of Production 4

Production of the Vaccine Using Fermenter Technology

For cultivating the *Candida* and *Propionibacterium acnes* strains of the invention on a large scale (250 and 200 liters, respectively), a special bioreactor with controlled cultivating conditions, such as e.g. APPLIKON ADI, 270 liters, was used.

The *Candida* vaccine strains of the invention, were cultivated separately in sterile modified Sabouraud medium with a pH of 5.8 to 7.2. To inoculate the culture medium, newly prepared cultures of the respective *Candida* strain were used. The strains were cultivated at a controlled temperature of 23 to 27° C. under aerobic conditions for 16 to 24 hours, until optimum growth was reached (determined by OD-measurement at 605 nm using a spectrometer, in Br).

The cellular mass was isolated from the medium by industrial ultrafcentrifugation or ultrafiltration.

Further steps were identical to the static method described in Examples 1 to 3 using agar.

The *Propionibacterium acnes* strain was cultivated in a sterile fluid modified Reinforced Clostridial Medium also in a bioreactor at a pH of 6.4 to 7.2. To inoculate the culture medium, a newly prepared *Propionibacterium acnes* strain was used. Cultivation was carried out under strict anaerobic conditions at a controlled temperature of 35 to 30° C. for 15 to 17 hours. The cellular mass was isolated by industrial ultracentrifugation or ultrafiltration.

Further steps were identical to the static method described in Examples 1 to 3 using agar.

EFFICACY IN THE MOUSE MODEL

Example 1

Immunostimulating Activity of the Vaccine of the Invention

A study of liver and spleen weight and total weight in laboratory mice vaccinated with *Propionibacterium acnes* CCM 7083, *Candida glabrata* CCM 8356, *Candida albicans* CCM 8355 and *Candida krusei* CCM 8357 was conducted in comparison with non-vaccinated control laboratory animals to demonstrate the immunostimulating activity of the vaccine as follows.

Vaccination: dose of 0.5 ml containing 0.75 mg of the *Propionibacterium acnes* strain CCM 7083, 0.25 mg of the *Candida glabrata* strain CCM 8356, 0.25 mg of the *Candida albicans* strain CCM 8355 and 0.25 mg of the *Candida krusei* strain CCM 8357.

Route of administration: intraperitonal

Animal species: female white laboratory mice (outbred HAN:ICR)

Number: 110

Weight: on average 30 g (84-day-old mice)

Number of animals in vaccinated groups: 11

Number of animals in control groups: 11

Methodology: Sacrificing and dissection of one vaccinated and one non-vaccinated (control) group of mice is performed at regular intervals of 0, 15, 30, 45 and 60 days. Liver weight, spleen weight and total weight are determined separately. The experiment is ended 60 days following administration. The vaccinated mice should be back to normal as compared with the non-vaccinated laboratory mice after 6 weeks.

Following the administration of the *Propionibacterium acnes* strain, the *Candida glabrata* strain, the *Candida albicans* strain and the *Candida krusei* strain to the mice, the vaccinated mice displayed a significant increase of liver and spleen weight as compared with the control mice, which did not receive a dose of the strains of the invention (see Table 1, below), thus demonstrating the immunostimulating activity of the vaccine of the invention.

Liver restored its normal weight on the $30^{th}$ day and spleen on about the $45^{th}$ day following the administration of the strains.

TABLE 1

Summary of the results of Example 1

| Day after administration | Liver | | Spleen | | Total weight (g) | |
|---|---|---|---|---|---|---|
| | vaccinated mice | control mice | vaccinated mice | control mice | vaccinated mice | control mice |
| 0 (before admin.) | − | − | − | − | − | − |
| 15th day | + | − | + | − | − | − |
| 30th day | − | − | + | − | − | − |
| 45th day | − | − | − | − | − | − |
| 60th day | − | − | − | − | − | − |

Explanations:
+ significant increase of organ weight as compared with control animals
− non-significant increase of organ weight as compared with control animals Example 2

Challenge Test Using the Formulation of Production Example 1

Method:

Forty C3H/HeJ mice weighing from 15 to 18 g were used for the test. The mice were divided into four test groups:

1st control group—10 mice—no vaccination and no challenge

2nd control group of 10 mice vaccinated with the following formulation of the invention for capsules for human use (i.e. CANDIVAC capsules ad us. hum., Production Example 1) in a dose of 0.5 ml p.o. (one dose per mouse is 0.5 ml with 1.5 mg dissolved test strains—0.75 mg of the *Propionibacterium acnes* strain; 0.25 mg of the *Candida albicans* strain; 0.25 mg of the *Candida glabrata* strain and 0.25 mg of the *Candida krusei* strain). The vaccine was administered to the animals of this group on days 0, 7 and 14. Twenty-four hours after the last dose, the animals were administered subcutaneously a dose of 0.2 ml of the challenge bacteria strain *Francisella tularensis* containing $1.5 \times 10^{4.0}$ bacteria (100 MLD$_{50}$).

3rd group of 10 mice—identical to group 2, the vaccine, however, being administered intraperitoneally in a dose of 0.5 ml.

4th group of 10 mice—control group to which only the challenge bacteria strain *Francisella tularensis* was administered in a dose of $1.5 \times 10^{4.0}$ (100 MLD$_{50}$).

After the challenge with *Francisella tularensis*, all animals were monitored for 28 days and morbiditiy and mortality of the test mice were recorded.

Results:

The vaccine CANDIVAC caps. ad us. hum. in accordance with Production Example 1 significantly increased the survival rate of mice after p.o. application (80% of the mice survived) and i.p. application (90% of the mice survived) as compared with the non-vaccinated control mice (mortality of 100%) and, thus, provided protection.

The results are summarised in Table 2 below.

TABLE 2

Results of the challenge test

| Group No | Number of mice | Vaccination | Challenge *Francisella tularensis* | Number of surviving mice (pc/%) | Number of dead mice (pc/%) | Mortality |
|---|---|---|---|---|---|---|
| 1 | 10 | — | — | 10 pc (100%) | 0 pc (0%) | No death |
| 2 | 10 | 0.5 ml p.o. | 100 MLD$_{50}$ | 8 pc (80%) | 2 pc (20%) | Death of mice on 12th and 13th day after infection |
| 3 | 10 | 0.5 ml i.p. | 100 MLD$_{50}$ | 9 pc (90%) | 1 pc (10%) | Death on 13th day after infection |
| 4 | 10 | — | 100 MLD$_{50}$ | 0 pc (0%) | 10 pc (100%) | Death between 7th and 11th day after infection |

Example 3

Blastic Transformation Test of the Vaccine According to the Invention

Test Method:

The BALB/c mice were administered a preparation corresponding to the formulation of the invention for oral capsules for human use (i.e. CANDIVAC caps. ad us. hum., Production Example 1) on days 0, 7 and 14 of the test i.p. and s.c. The control group was applied buffered saline.

Part of the animals was sacrificed 24, 48, 72 hours, 5 and 7 days after the administration of the last dose. Cell suspensions were prepared from the obtained spleens and diluted to a concentration of $4 \times 10^6$ cells per 1 ml culture medium. 20 µl of this cell suspension and 50 µl mitogen each were transferred with a pipette into the wells of the test kit. ConA was used in a concentration of 2 μl/1 ml medium and LPS (lipopolysaccharide) in a concentration of 20 μl/1 ml medium. The specific antigens of the vaccine CANDIVAC were used in a concentration of 100 μl/1 ml medium. The cells and mitogens were incubated for 67 hours at 37° C. at 5% $CO_2$. Subsequently, 50 μg marked thymidin (1μ Ci per well) was added. The test plates were incubated for further 5 hours at 37° C., 5% $CO_2$ and 100% atmospheric humidity. After the collection of the cells by means of a harvester Flow, the cells were transferred into vials containing scintillation fluid and radioactivity (β-radiation) was measured using a Rackbeta computer and expressed in cpm.

Results:

Both routes of administration of the vaccine CANDIVAC enhance cell proliferation almost at all time intervals, only on day 7 after the p.o. administration, there is no statistically significant increase of cell proliferation.

Test Method

Different ratios of the *Candida* strains of the invention and the *Propionibacterium* strain of the invention were used to prepare a vaccine.

5 mg dry matter of the vaccine strains in different ratios were dissolved in 1 ml PBS pH 7.2.

The vaccine compositions prepared in this way were administered intraperitoneally to female outbred SPF-ICR mice having a weight of 16 to 20 g (5 mice, 0.2 ml each). Ten days later, the animals were killed with chloroform and dissected. The increase of liver and spleen weight was determined and substantiated histologically. A group of 2 mice to which only PBS was administered intraperitonially served as control group. The results of the weight increase were evaluated statistically using a non-parametric U-test.

The histologic examination of liver and spleen was carried out by means of a paraffin method and hematoxylin-eosin staining.

TABLE 3

Test results of blastic transformation of spleen cells after administration of the vaccine according to the invention

| In vitro stimulation | Medium (PBS) | | ConA 5 μg/ml | | LPS 20 μg/ml | | CANDIVAC 100 ConA 5 μg/ml | |
|---|---|---|---|---|---|---|---|---|
| | per os | i.p. | per os | i.p. | per os | i.p. | per os | i.p. |
| Day 1 | 3.18** | 2.77** | 0.97 | 1.77** | 2.53** | 0.52** | 5.86** | 4.24** |
| Day 2 | 1.89* | 3.84** | 1.23* | 0.85* | 1.27 | 0.57* | 4.94** | 5.32* |
| Day 3 | 2.67** | 2.78** | 0.71 | 0.39 | 1.63** | 0.65** | 2.33** | 7.44** |
| Day 5 | 1.27 | 3.24* | 0.72* | 0.59* | 1.34* | 0.79 | 2.35** | 8.53** |
| Day 7 | 1.87* | 3.36 | 0.83 | 0.74 | 2.80** | 0.54** | 0.57 | 7.80** |

**$p < 0.01$
*$p < 0.05$

Table 3 shows the basal lymphoproliferation of spleen cells (referred to as medium) and the proliferation of splenocytes after in vitro stimulation with ConA, LPS and the vaccine of the invention. The results are indicated in form of transformation index, ratio of lymphoproliferation of cells of vaccinated mice and control mice.

Determination of the Ratio of the Individual Strains—*Candida albicans* (CCM 8355), *Candida glabrata* (CCM 8356), *Candida krusei* (CCM 8357) and *Propionibacterium acnes* (CCM 7083)—According to the Invention in the Vaccine of the Invention in an Animal Model (Mice)

14 days after the vaccination, the three remaining vaccinated animals per group and 3 non-vaccinated control animals were challenged by means of intravenous application of living *Candida albicans* in a total dose of 104.0 of living *Candida* cells of *Candida albicans* per mouse. All test animals (vaccinated and non-vaccinated mice) were sacrificed four weeks after the challenge assay and were examined for living cells of the *Candida albicans* strains.

The vaccine is only considered protective if it is not possible to isolate a *Candida albicans* strain from the kidneys and cultivate it.

TABLE 4

Impact of the ratio of the vaccine strains *Candida albicans* (CCM 8355), *Candida glabrata* (CCM 8356), *Candida krusei* (CCM 8357) and *Propionibacterium acnes* (CCM 7083) (CA = a1, CG = a2, CK = a3, PA = a4) on the protective activity and safety of the vaccine produced thereof

| Composition of the vaccine | Statistically significant ($p \leq 0.05$) weight increase | | Histological immuno-mudulating effect | | Protective activity of the vaccine against *Candida albicans* | Safety | Result |
|---|---|---|---|---|---|---|---|
| | Liver | Spleen | Liver | Spleen | | | |
| 1. a1:a2:a3:a4 = 10-20:10-20:10-20:40-70 | + | + | + | + | + | safe | conform |
| 2. a1:a2:a3:a4 = 15-20:15-20:15-20:40-55 | + | + | + | + | + | safe | conform |

TABLE 4-continued

Impact of the ratio of the vaccine strains *Candida albicans* (CCM 8355), *Candida glabrata* (CCM 8356), *Candida krusei* (CCM 8357) and *Propionibacterium acnes* (CCM 7083) (CA = a1, CG = a2, CK = a3, PA = a4) on the protective activity and safety of the vaccine produced thereof

| Composition of the vaccine | Statistically significant ($p \leq 0.05$) weight increase | | Histological immuno-mudulating effect | | Protective activity of the vaccine against *Candida albicans* | Safety | Result |
|---|---|---|---|---|---|---|---|
| | Liver | Spleen | Liver | Spleen | | | |
| 3. a1:a2:a3:a4 = 10-15:10-15:10-15:55-70 | + | + | + | + | + | safe | conform |
| 4. a1:a2:a3:a4 = 10:10:10:70 | + | + | + | + | + | safe | conform |
| 5. a1:a2:a3:a4 = 15:15:15:55 | + | + | + | + | + | safe | conform |
| 6. a1:a2:a3:a4 = 20:20:20:40 | + | + | + | + | + | safe | conform |
| 7. a1:a2:a3:a4 = 5:5:5:85 | + | + | + | + | − | safe | not conform |
| 8. a1:a2:a3:a4 = 1:1:1:97 | + | + | + | + | − | safe | not conform |
| 9. a1:a2:a3:a4 = 25:25:25:25 | − | + | − | + | − | safe | not conform |
| 10. a1:a2:a3:a4 = 30:30:30:10 | − | − | − | − | − | safe | not conform |

The results in Table 4 show that optimum results with respect to the protective activity and safety of the vaccine are obtained as long as the ratio of the 4 vaccine strains (*Candida albicans* CCM 8355=a1; *Candida glabrata* CCM 8356=a2; *Candida krusei* CCM 8357=a3; *Propionibacterium acnes* CCM 7083=a4) according to the invention is as follows:

1. a1:a2:a3:a4=10-20:10-20:10-20:40-70
2. a1:a2:a3:a4=15-20:15-20:15-20:40-55
3. a1:a2:a3:a4=10-15:10-15:10-15:55-70
4. a1:a2:a3:a4=10:10:10:70
5. a1:a2:a3:a4=15:15:15:55
6. a1:a2:a3:a4=20:20:20:40

The vaccine compositions 7, 8, 9 and 10 did not show protective activity in the challenge assay with living *Candida* strains.

Compositions 7 and 8 showed unspecific immunity due to the high *Propionibacterium acnes* amount. It was not possible to obtain specific protection against *Candida*. Compositions 9 and 10 showed an insufficient form of unspecific and specific immunity.

Confirmation of the Protective Activity of the Vaccine of the Inventions Prepared from the Strains *Candida albicans* (CCM 8355), *Candida glabrata* (CCM 8356), *Candida krusei* (CCM 8357) and *Propionibacterium acnes* (CCM 7083) in Women TABLE 5a Vaginal application

| Result of treatment | Number of patients | % | Period of observation (months) Average | Range |
|---|---|---|---|---|
| Excellent | 6 | 54.5 | 9.7 | 2-13 |
| Good | 3 | 27.3 | 11.3 | 10-12 |
| Satisfactory | 0 | 0 | — | — |

TABLE 5a-continued

Vaginal application

| Result of treatment | Number of patients | % | Period of observation (months) Average | Range |
|---|---|---|---|---|
| Indifferent | 2 | 18.2 | 12.0 | 12 |
| Total | 11 | 100.0 | — | — |

TABLE 5b

Oral application

| Result of treatment | Number of patients | % | Observation period (months) Average | Range |
|---|---|---|---|---|
| Excellent | 24 | 58.5 | 10.2 | 7-16 |
| Good | 9 | 21.9 | 11.0 | 7-16 |
| Satisfactory | 4 | 9.8 | 7.0 | — |
| Indifferent | 4 | 9.8 | 7.3 | 2-11 |
| Total | 41 | 100.0 | — | — |

TABLE 5c

Simultaneous vaginal and oral application

| Result of treatment | Number of patients | % | Observation period (months) Average | Range |
|---|---|---|---|---|
| Excellent | 5 | 35.7 | 8.6 | 6-11 |
| Good | 5 | 35.7 | 14.0 | 12-18 |

TABLE 5c-continued

Simultaneous vaginal and oral application

| Result of treatment | Number of patients | % | Observation period (months) | |
|---|---|---|---|---|
| | | | Average | Range |
| Satisfactory | 2 | 14.3 | 7.0 | 5-9 |
| Indifferent | 2 | 14.3 | 6.0 | 3-9 |
| Total | 14 | 100.0 | — | — |

The results shown above demonstrate that the vaccine of the invention provided excellent protective activity in the majority of patients, a fact that is of particular importance, given the problematic nature of a *Candida* infection, which often has a chronic course, can become systemic and, consequently, is very difficult to treat.

EXAMPLES OF APPLICATION IN HUMAN MEDICINE

Example of Application 1

Vaginal Suppositories

After visiting a swimming pool, a 34-year-old woman suffered from an inflammatory vaginitis (itching, burning, discharge), which was presumably caused by fungi. Treatment with *Candida* suppositories according to Production Example 2 was carried out—one vaginal suppository every evening on 5 consecutive days. After one day, there was a slight improvement of the ailments, after 4 days, the patient was free of ailments.

Example of Application 2

Vaginal Suppositories

After being administered antibiotics, a 47-year-old female patient suffered repeatedly from fungal vaginitis. The treatment with 7 suppositories of *Candida* vaccine according to Production Example 2 on 5 consecutive days (in the evening, vaginal) resulted in an improvement after 2 days, after 5 days, the patient was free of ailments. As further treatment with antibiotics was to be expected, the woman was administered another course of 7 capsules 4 weeks and 8 weeks later, respectively. An administration of antibiotics after 10 weeks did not lead to a recurrence of the vaginitis.

Example of Application 3

Rectal Suppositories

A 24-year-old patient suffered from severe ailments caused by hemorrhoids. Despite a sclerotherapy, he still suffered from ailments caused by itching and burning in the anal region, which suggested presence fungi in the rectum. After 2-3 days, the treatment with 10 rectal suppositories according to Production Example 3 (on 10 consecutive days, in the evening, rectal) resulted in a considerable improvement of the ailments, which were still present after 6 weeks.

Example of Application 4

Capsules for Oral Application

Due to leukopenia, a 61-year-old-patient suffered from recurring oral thrush—Ampho-Moronal (amphothericin B) was almost ineffective due to repeated application.

The administration of 5 capsules of *Candida* vaccine according to Production Example 1 resulted in an improvement of the ailments after 5 days. The administration of 2 further cycles of 5 days each—4 and 8 weeks later—kept the ailments on a level that was tolerable for the patient in spite of the fact that the basic disease persisted.

Example of Application 5

Capsules

A 72-year-old female patient kept suffering from unspecific ailments in the gastrointestinal tract, e.g. stool irregularities, diarrhea, flatulence and unwellness. Severe organic disorders were excluded from a medical point of view; fungi in the intestine seemed to be likely. Already after one cycle, a three-month treatment with *Candida* capsules according to Production Example 1 (on ten consecutive days at the beginning of each month, administration of one capsule per day, in the morning) resulted in a considerable improvement, after 3 cycles the ailments had almost ceased.

EXAMPLES OF APPLICATION IN VETERINARY MEDICINE

Furthermore, the vaccine of the invention can also be used and is effective in veterinary medicine. Its application will be particularly advantageous with small animals, such as cats and dogs.

As becomes clear from the above statements and examples of application, the present invention, thus, provides a highly effective and, in addition, readily applicable vaccine for the immunoprophylaxis and the treatment of candidamycoses in veterinary and human medicine. In human medicine, the vaccine of the invention can be applied orally, parenterally as well as locally, in particular vaginally and rectally. In this case, oral, vaginal and rectal application is particularly preferred. Moreover, the vaccine of the invention can be applied parenterally, locally or orally in veterinary medicine.

Thus, a readily applicable and well-tolerated vaccine for the effective immunoprophylaxis and therapy of candidamycoses for use in human and veterinary medicine is provided. Moreover, due to the preferred oral or local application, the risk of a possible anaphylactic or anaphylactoid reaction is excluded.

The invention claimed is:

1. A vaccine comprising a combination of vaccine strains, wherein the combination consists of formaldehyde-inactivated *Candida albicans* strain CCM 8355, formaldehyde-inactivated *Candida glabrata* strain CCM 8356, and formaldehyde-inactivated *Candida krusei* strain CCM 8357 and heat-inactivated *Propionibacterium acnes* strain CCM 7083 in the ratio of 10-20:10-20:10-20:40-70.

2. The vaccine of claim 1, wherein the ratio is 15-20:15-20:15-20:40-55.

3. The vaccine of claim 1, wherein the ratio is 10-15:10-15:10-15:55-70.

4. The vaccine of claim 1, wherein the total dry weight of all the vaccine strains is 2 to 10 mg per dose.

5. The vaccine of claim 1, wherein the vaccine comprises less than 0.02% formaldehyde by weight.

6. The vaccine of claim 1, wherein the vaccine is for oral, local, or parenteral administration.

7. The vaccine of claim 6, wherein the vaccine is for topical, vaginal, or rectal administration.

8. The vaccine of claim 6, wherein the vaccine is for oral administration and the ratio is 10:10:10:70.

9. The vaccine of claim 6, wherein the vaccine is for vaginal administration and the ratio is 15:15:15:55.

10. The vaccine of claim 6, wherein the vaccine is for rectal administration and the ratio is 20:20:20:40.

11. The vaccine of claim 1, wherein the vaccine is formulated in the form of a capsule, tablet, lozenge, pastille, syrup, oral suspension, oral emulsion, globulus, pill, suppository, vaginal ovule, ampoule, prefilled syringe, aerosol, insufflation, or mouthwash.

12. The vaccine of claim 1, wherein the vaccine is for use against local candidiasis, cutaneous candidiasis, or mucocutaneous candidiasis.

13. The vaccine of claim 1, wherein the local candidiasis affects the outer mucosa of the genital tract, the urogenital tract, the oral cavity, the gastrointestinal tract, or the skin.

14. The vaccine of claim 12, wherein the vaccine is for use against stomatitis (thrush) or vaginitis.

15. The vaccine of claim 1, wherein the vaccine further comprises one or more carriers or excipients suitable for veterinary administration.

16. The vaccine of claim 1, wherein the vaccine further comprises one or more carriers or excipients suitable for human administration.

17. The vaccine of claim 1, wherein the vaccine protects an animal against challenge with a *Candida albicans* strain, wherein the protection is measured by lack of isolation of the *Candida albicans* strain from kidneys of the animal.

18. A method of preparing the vaccine of claim 1 comprising the steps of:
    (a) separately cultivating the *Candida albicans* strain CCM 8355, the *Candida glabrata* strain CCM 8356, and the *Candida krusei* strain CCM 8357;
    (b) inactivating the *Candida albicans* strains with formaldehyde;
    (c) heat-inactivating the *Propionibacterium acnes* strain CCM 7083;
    (d) lyophilizing each of the inactivated strains; and
    (e) mixing the lyophilized inactivated strains of the *Candida albicans* strain CCM 8355, the *Candida glabrata* strain CCM 8356, the *Candida krusei* strain CCM 8357, and the *Propionibacterium acnes* strain CCM 7083 in the ratio 10-20:10-20:10-20:40-70 to obtain the vaccine.

19. The method of claim 18, wherein the total dry weight of all the vaccine strains is 2 to 10 mg per dose.

20. The method of claim 18, wherein the formaldehyde content of the vaccine is less than 0.02% by weight.

21. The method according to claim 18, wherein the vaccine strains are cultivated on a large scale in fermenters.

22. The method of claim 18, further comprising the step of mixing the lyophilized vaccine strains with one or more excipients.

23. The method according to claim 18, wherein the *Candida albicans* strains are cultivated on glucose peptone agar or Sabouraud's agar at 23° to 27° C. for 48 to 72 hours, or at 35° C. to 39° C. for 22 to 27 hours under aerobic conditions at a pressure of 0.1 to 0.2 bar and 90% to 98% atmospheric humidity and wherein the cells of the cultivated strains are subsequently washed with sterile water and disintegrated in three freeze and thaw cycles.

24. The method according to claim 18, wherein the *Candida albicans* strains are cultivated in Sabouraud's culture medium at 37° C. for 24 to 48 hours under aerobic conditions and the cells of the cultivated strains are subsequently isolated using an ultrafiltration cartridge with a cut-off of 300 kDa followed by purification through repeated washing with sterile physiological saline, centrifugation at 4,500 g, washing with sterile water, and disintegration in three freeze and thaw cycles.

25. The method according to claim 18, wherein the *Propionibacterium acnes* strain is cultivated on a blood agar, reinforced clostridial agar, or Viande-Levure (VL) agar containing blood at 35° C. to 39° C. for 46 to 50 hours under strictly anaerobic conditions at 90% to 98% atmospheric humidity, followed by lysis of cells of the *Propionibacterium acnes* with sterile distilled water, extraction at 2° C. to 8° C. for 22 to 26 hours, and inactivation by heating up to three times to 56° C. to 62° C. for at least one hour at an interval of at least 24 hours.

26. The method of claim 18, wherein the *Propionibacterium acnes* strain is cultivated in a reinforced clostridial medium at 35° C. to 39° C. for 46 to 50 hours under strictly anaerobic and static conditions and the cells of the *Propionibacterium acnes* strain are isolated using an ultrafiltration cartridge with a cut-off of 300 kDa followed by purification through repeated washing with sterile physiological saline and centrifugation at 4,500 g, lysis of the cells with sterile distilled water, extraction at 2° C. to 8° C. for 22 to 26 hours, and inactivation by heating up to 56° C. to 62° C. for at least one hour at an interval of at least 24 hours.

27. The method according to claim 21, wherein the *Candida albicans* strains are cultivated in Sabouraud's culture medium having a pH of 5.6 to 7.2 at a temperature of 23° C. to 27° C. for 16 to 24 hours under aerobic conditions with 15% to 20% dissolved oxygen at a pressure of 0.1 to 0.2 bar against atmospheric pressure under addition of filtered atmospheric air at 40 to 50 rpm and the strains are isolated by means of industrial ultracentrifugation at 3,600 to 5,300 g, ultracentrifugation by means of an ultracentrifugation cartridge with a cut-off of 300 kDa, or a combination thereof.

28. The method according to claim 21 or 27, wherein the *Propionibacterium acnes* strain is cultivated in reinforced clostridial medium having a pH of 6.4 to 7.2 and a temperature of 35 to 39° C. for 15 to 17 hours under strict anaerobic conditions with a maximum of 1% dissolved oxygen at a pressure of 0.1 to 0.2 bar against atmospheric pressure under addition of 10 L of a filtered mixture of $N:CO_2$ (1:2) per minute at 40 to 50 rpm and the strain is isolated by means of industrial ultracentrifugation at 3,600 to 5,300 g, ultrafiltration by means of an ultrafiltration cartridge with a cut-off of 300 kDa, or a combination thereof.

* * * * *

UNITED STATES PATENT AND TRADEMARK OFFICE
CERTIFICATE OF CORRECTION

PATENT NO. : 7,648,698 B2  Page 1 of 1
APPLICATION NO. : 11/574808
DATED : January 19, 2010
INVENTOR(S) : D. Braun et al.

It is certified that error appears in the above-identified patent and that said Letters Patent is hereby corrected as shown below:

| COLUMN | LINE | ERROR |
|---|---|---|
| (30) Pg. 1, col. 1 | Foreign Application Priority Data | "10 204 046.391" should read --10 204 046.391.3-- |

Signed and Sealed this

Twentieth Day of July, 2010

David J. Kappos
*Director of the United States Patent and Trademark Office*